US012667330B2

(12) United States Patent
Tek

(10) Patent No.: US 12,667,330 B2
(45) Date of Patent: Jun. 30, 2026

(54) MULTI-PLANE-BASED CARDIAC WALL MOTION DETECTION IN MEDICAL ULTRASOUND

(71) Applicant: Siemens Medical Solutions USA, Inc., Malvern, PA (US)

(72) Inventor: Huseyin Tek, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 171 days.

(21) Appl. No.: 18/352,577

(22) Filed: Jul. 14, 2023

(65) Prior Publication Data

US 2025/0017557 A1 Jan. 16, 2025

(51) Int. Cl.
A61B 8/08 (2006.01)
A61B 8/00 (2006.01)

(52) U.S. Cl.
CPC ............ A61B 8/0883 (2013.01); A61B 8/463 (2013.01); A61B 8/485 (2013.01)

(58) Field of Classification Search
CPC ................................ A61B 8/463; A61B 8/485
See application file for complete search history.

(56) References Cited

U.S. PATENT DOCUMENTS

| | | | |
|---|---|---|---|
| 7,421,101 B2 | 9/2008 | Georgescu et al. | |
| 7,860,290 B2 | 12/2010 | Gulsun et al. | |
| 7,953,266 B2 | 5/2011 | Gulsun et al. | |
| 7,990,379 B2 | 8/2011 | Aharon et al. | |
| 8,073,227 B2 | 12/2011 | Gulsun et al. | |
| 8,170,304 B2 | 5/2012 | Tek et al. | |
| 9,129,417 B2 | 9/2015 | Zheng et al. | |
| 10,354,744 B2 | 7/2019 | Sharma et al. | |
| 10,792,009 B2 | 10/2020 | Ohuchi et al. | |
| 10,827,982 B2 | 11/2020 | Sitek | |
| 10,881,379 B2 | 1/2021 | Villain et al. | |
| 11,450,000 B2 | 9/2022 | Upton et al. | |
| 2002/0072674 A1* | 6/2002 | Criton et al. ............ A61B 8/12 |
| 2005/0059876 A1* | 3/2005 | Krishnan et al. ........ A61B 5/05 |
| 2008/0077013 A1* | 3/2008 | Kawagishi .......... G01S 7/52074 |
| | | | 600/443 |
| 2009/0112088 A1 | 4/2009 | Ohuchi et al. | |
| 2009/0238404 A1 | 9/2009 | Orderud et al. | |
| 2010/0041992 A1* | 2/2010 | Ohuchi et al. .......... A61B 8/14 |

(Continued)

FOREIGN PATENT DOCUMENTS

| | | |
|---|---|---|
| JP | 2004514527 A | 5/2004 |
| JP | 2007526016 A | 9/2007 |

(Continued)

OTHER PUBLICATIONS

Extended European Search Report (EESR) mailed Nov. 22, 2024 in corresponding European Patent Application No. 24188365.1.

*Primary Examiner* — Joseph M Santos Rodriguez
*Assistant Examiner* — Kaitlyn Eunji Kim

(57) ABSTRACT

To improve the data quality in detecting cardiac wall motion, regions of abnormal wall motion are detected from a view. The scan settings are then changed to focus scanning on each region, providing improved data such as data with more speckle being present. The scan settings may include changing an orientation of the scan plane, reducing out-of-plane motion, and/or increasing speckle content. The improved data is used to more accurately determine strain.

20 Claims, 3 Drawing Sheets

(56)     References Cited

U.S. PATENT DOCUMENTS

| | | | |
|---|---|---|---|
| 2019/0298303 A1* | 10/2019 | Bingley .................... | A61B 8/54 |
| 2020/0093370 A1* | 3/2020 | Abe ..................... | A61B 5/1128 |
| 2020/0214662 A1* | 7/2020 | Konofagou et al. ..... | A61B 8/08 |
| 2021/0015456 A1* | 1/2021 | Chiang et al. ........... | A61B 8/00 |
| 2021/0280298 A1* | 9/2021 | Samset et al. ......... | G16H 30/40 |
| 2021/0287361 A1* | 9/2021 | Shriram et al. | |
| 2022/0142612 A1* | 5/2022 | Weber ..................... | A61B 8/54 |
| 2022/0192627 A1* | 6/2022 | Quattrone-Brown et al. ............. | |
| | | | A61B 8/08 |

FOREIGN PATENT DOCUMENTS

| | | | |
|---|---|---|---|
| JP | 2009106548 A | 5/2009 | |
| JP | 2009226226 A | 10/2009 | |
| JP | 2010042151 A | 2/2010 | |
| JP | 2012187383 A | 10/2012 | |
| JP | 2013162921 A | 8/2013 | |
| JP | 2020520273 A | 7/2020 | |
| JP | 2021507433 A | 2/2021 | |
| JP | 2021102064 A | 7/2021 | |
| WO | 2002045587 A1 | 6/2002 | |
| WO | 2005001769 A2 | 1/2005 | |

* cited by examiner

100 — Scan View/Plane

110 — Detect Any Abnormal Wall Motion Regions

120 — Scan Patch at Abnormality with Different Settings

130 — Select Settings (e.g., Plane) with Improved Data

140 — Determine Strain using Improved Data

150 — Output Strain

320

224

300

310

420 — Display        ECG — 430

400 — Ultrasound Scanner

Image  402
Processor

Memory
404

Input — 406

408 — BF

ML  405
Model

410 — XDCR

MULTI-PLANE-BASED CARDIAC WALL MOTION DETECTION IN MEDICAL ULTRASOUND

BACKGROUND

The present embodiments relate to medical ultrasound imaging. In particular, cardiac wall motion analysis is performed using ultrasound.

Two-dimensional (2D) B-mode echocardiography provides important information about heart operation, such as volumes, diastolic function, right ventricular function, hemodynamics, and valvular regurgitation. In addition, detection of heart failure is facilitated by the assessment of global longitudinal strain and regional strains in the heart wall. Myocardial mechanics, ischemic heart disease, cardiomyopathies, left ventricular (LV) diastolic dysfunction, and subclinical myocardial dysfunction may be detected in patients.

In current clinical tools, a sonographer obtains multiple standard views of the heart chamber, such as A2C, A3C, A4C, and longitudinal views, while optimizing image quality, maximizing frame rate, and minimizing foreshortening, which are all critical to reduce measurement variability. Global and segmental strains of each view are calculated by first creating an initial contour at the myocardium border and then this contour is tracked to all frames using speckle. A 17-segment bulls-eye model (or 16 or 18 segment) is constructed from the six segmental strains of each view. Specifically, a quantitative wall motion score can be assigned to each segment. A four-grade scoring is usually applied based on the segment model: (1) normal or hyperkinetic, (2) hypokinetic (3) akinetic and (4) dyskinetic.

Unfortunately, the semiquantitative wall motion score of each segment may not be always reliable. Accuracy of segmental strains may be negatively affected by issues in speckle tracking due to the poor imaging in certain locations. It may be challenging to select one set of acquisition parameters that results in capturing wall motion in all areas of a standard view. It may be difficult to track speckle if significant motion is in the out-of-plane direction in certain locations.

BRIEF SUMMARY

By way of introduction, the preferred embodiments described below include methods, systems, and non-transitory computer readable media for detecting cardiac wall motion. To improve the data quality, regions of abnormal wall motion are detected from a view. The scan settings are then changed to focus scanning on each region, providing improved data such as data with more speckle being present. The scan settings may include changing an orientation of the scan plane, reducing out-of-plane motion, and/or increasing speckle content. The improved data is used to more accurately determine strain.

In a first aspect, a method is provided for detecting cardiac wall motion with a medical ultrasound scanner. The medical ultrasound scanner first scans, using first values of scan settings, a first plane through a heart of a patient. The first plane is scanned at different times, providing first ultrasound data representing the heart at the different times. Abnormal wall motion is detected from the first ultrasound data. The medical ultrasound scanner second scans, using second values of the scan settings, a region of the abnormal wall motion in a second plane. The second settings are different than the first values of the scan settings. The second plane is different than the first plane, and the second scanning results in second ultrasound data. Strain is determined for the abnormal wall motion from the second ultrasound data. An image representing the strain.

In one embodiment, a standardized view of the heart is first scanned. The second scan with a smaller field of view just covering the region of the abnormal wall motion, the region less than a field of view of the standardized view.

In another embodiment, a machine-learned model detects the abnormal wall motion.

Various scan settings may be changed in the scanning, such as gain, contrast, depth, and/or field of view. For example, the field of view for the first scan is for an entire heart area (larger field of view), and the field of view for the second scanning being a smaller field of view for a region about the abnormal motion. The scan settings may include the orientation of the plane, such as changing scan settings to re-orient from the first plane to the second plane. In one example, the scan settings for the second scanner configure the medical ultrasound scanner for generating speckle.

According to one embodiment, the second plane is selected based on a level of scatter and/or amount of relative motion of the cardiac wall. The region of abnormality may be scanned along different planes, and one of the planes selected as more optimum as compared to other planes.

As one embodiment, the strain is determined for a segment of a multi-segment model. The multi-segment model including the strain is displayed. As another embodiment, the strain is determined in multiple dimensions for the first and second planes. A multi-dimensional strain map is displayed.

The second scanning and determination of strain may be repeated for different regions corresponding to different locations of abnormal wall motion. The first scanning, detection of abnormal wall motion, second scanning, and determination of strain may be repeated for different views (e.g., different standardized views) of the heart. The strains from the different standardized views are then displayed.

In a second aspect, an ultrasound system is provided for detecting cardiac wall motion. An ultrasound scanner is configured to detect a location of abnormality of the cardiac wall motion for a patient, scan the location with different values of one or more settings, and determine strain of the cardiac wall motion at the locations from ultrasound data from the scan using at least one of the different values of the one or more settings. A display is configured to display an image of the strain.

In an embodiment, the one or more settings are for scan of different planes such that the ultrasound scanner is configured to scan the location in the different planes. In another embodiment, the one or more settings are gain, contrast, and/or depth such that the ultrasound scanner is configured to scan the location for imaging with different levels of speckle.

In another embodiment, the ultrasound scanner is configured to scan the heart of the patient in a standardized view, detect the location from the standardized view, and scan the location with a field of view less than the standardized view.

In a third aspect, a non-transitory computer readable storage medium has stored therein data representing instructions executable by a programmed processor for detecting cardiac wall motion. The storage medium includes instructions for: scanning a heart of a patient in a standardized view; detecting abnormal wall motion of the heart from the standardized view; acquiring B-mode data in a patch at the abnormal wall motion; determining strain from the B-mode data for the patch; and displaying a strain map including a first segment of the strain map having the strain determined from the B-mode data for the patch and a second segment of the train map having another strain determined from the standardized view.

According to an embodiment, the instructions for acquiring the B-mode data in the patch include acquiring the B-mode data with the patch being in a different plane than the standardized view. The instructions further include selecting the different plane based on an amount of speckle or motion.

As another embodiment, the instructions for acquiring the B-mode data include acquiring the B-mode data with a greater level of speckle in the patch than in the standardized view at a location of the abnormal wall motion.

In yet another embodiment, the instructions further comprise repeating the scanning, detecting, acquiring and determining for different standardized views. The instructions for displaying the strain map include displaying a 16, 17, or 18-segment bulls-eye view.

The following claims define the present invention, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Figure 1:
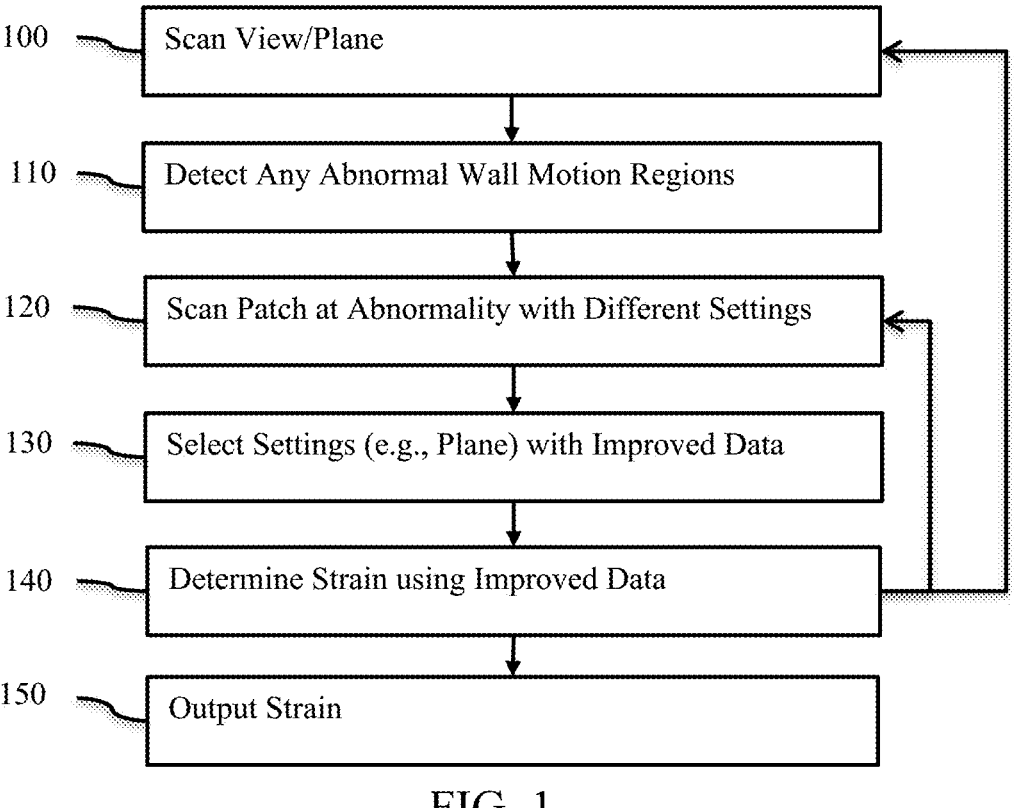
FIG. 1 is a flow chart of one embodiment of a method for detecting cardiac wall motion.

Tracking assisted acquisition is provided, such as for fusion of 2D B-mode echocardiography for 2D global and/or regional cardiac mechanics. A user is assisted in acquiring the best possible or sufficient B-mode echocardiography data for quantifying global and/or regional strains, such as by sampling in multi-planes about any regions of abnormal wall motion.

Automated solutions compute global and regional cardiac mechanics from 2B echo data. The strain analysis of these solutions strongly depends on image quality. One set of parameters or values of settings for the ultrasound scanner, such as gain settings, may not capture wall motion in all areas. For example, one or more gaps in the heart wall appear due to lack of speckle, shadowing, and/or other artifacts.

To assist users and/or the automated solution for better images in certain regions, patches are scanned with different values for the scan settings. The areas with abnormal wall motion, whether due to actual abnormality or due to poor scanning, are scanned again with different settings to improve the data by additional acquisition and/or to improve the data by better settings for scanning those locations. In one approach, the different settings are for scanning the region of abnormality along different scan planes. The field of view is shifted not just in area (smaller) and focus (in the region) but also in the plane being scanned. This multi-plane analysis of cardiac wall motion abnormalities from 2D echo may provide data usable for more accurate tracking and corresponding strain analysis. Improved data, and even a confidence measure, may be provided for tracking and image quality. The image quality is improved specifically in low confidence regions by changing acquisition parameters, such as rotating the probe slightly if necessary. The tracking may be run again only in the low confidence regions.

In one implementation, the sonographer is assisted during 2D B-mode echocardiography acquisition to obtain good quality data in patches and fuse results for strain analysis. When a sonographer acquires 2D B-Mode echocardiography image in a standard orientation view, such as A2C, the system first detects myocardium borders with abnormal wall motions and acquires (automatically or through user guidance) more data, e.g., only, for regions of abnormal wall motion by adjusting input parameters and orientation planes. The system, by automation and/or guidance to the sonographer, causes rotation of the probe in certain degrees and quantifies motion in multi-planes only the vicinity of abnormal wall motion in real time. Tracking is run, e.g., only, in these corrected regions. The resulting calculated strains are collected or fused with previously obtained results from other areas. The multi-plane system may result in more robust strain analysis as well as less inter and intra-user variability. The image quality is improved, especially for images acquired by less experienced sonographers. A framework is established for semi- or fully autonomous robotic device-based 2D B-mode echocardiography image acquisition.

FIG. 1 shows a method for detecting cardiac wall motion with a medical ultrasound scanner. The strain and/or other indicators of abnormal and/or normal movement or operation of the heart are detected. The detection relies on acquiring additional data with different settings, such as different field of view, gain, and/or scan plane, for regions that appear to have abnormal cardiac wall motion. By gathering this additional data with different values to configure scanning, improved ultrasound data is provided for strain or other analysis in those regions.

Figure 4:
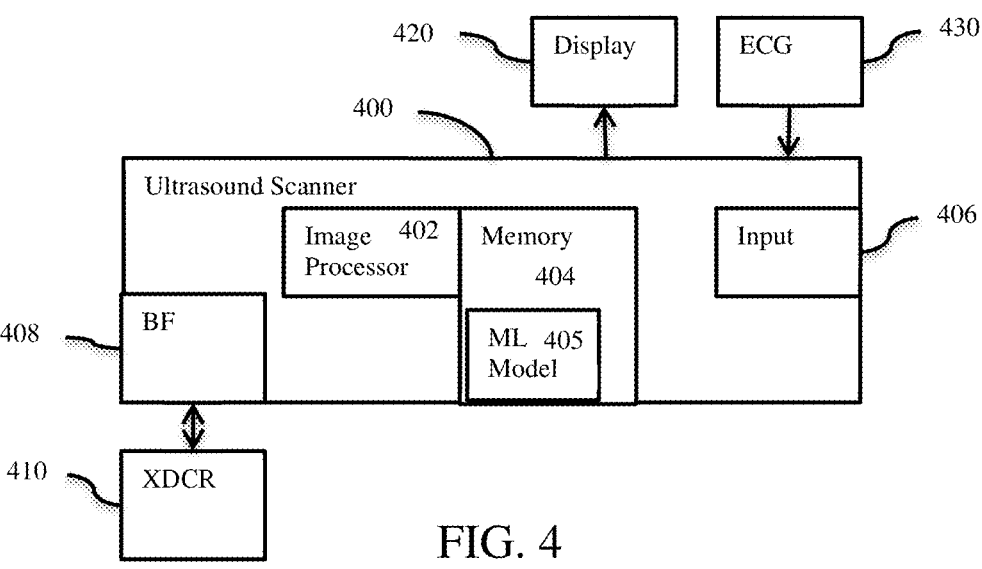
FIG. 4 is a block diagram of one embodiment of a system for detecting cardiac wall motion.

The method is performed by the system of FIG. 4, an ultrasound scanner, an image processor, or different systems or devices. In one embodiment, an ultrasound imaging system or medical ultrasound scanner performs the acts of FIG. 1. In other embodiments, a processor performs acts 110, 130, 140, and 150. An ultrasound scanner performs acts 100 and 120. A display may be used for act 150.

Additional, different, or fewer acts may be performed. For example, acts for determining volume flow, ejection fraction, information about heart operation, or other flow analysis of the heart are provided. As another example, acts for using the strain or other heart wall motion analysis are provided, such as for categorizing the condition of the heart, segment scoring, and/or for diagnosis. As another example, act 150 is not provided.

The acts are performed in the order shown (top to bottom or numerical) or a different order.

In act 100, the ultrasound scanner scans the heart of a patient. Using a transducer scanning through rib windows from the exterior of the patient, a trans-esophageal transducer scanning from within the throat of the patient, or an intra-cardiac echocardiography catheter scanning from within the heart, the heart of the patient is scanned in B-mode.

The scan is performed using values for scan settings. The values are for beamformer, transducer, image processing, and/or post processing. The values for the field of view (e.g., depth, width, and/or scan pattern), gain, contrast, frequency, and/or other settings or acquisition parameters for the scan of act 100 are set by the sonographer and/or are default values for cardiac imaging.

The values create a field of view that scans an area of the entire heart and/or a chamber of the heart. In one embodiment, the scan is for a standardized view of the heart, such as the longitudinal, A4C, A3C, or A2C view. The scan of act 100 may be for other standardized or non-standard views. The scan is 2D so is a scan along a plane through the heart.

The scanning of act 100 repeats to gather two or more images representing the heart of the patient at different times. For example, a sequence of five or more images per heart cycle is acquired. An ECG may be used to designate the timing relative to the heart cycle for the images. Gating or triggering may be used to acquire images at desired times of the heart cycle, such as end diastole (ED) and end systole (ES).

Figure 2:
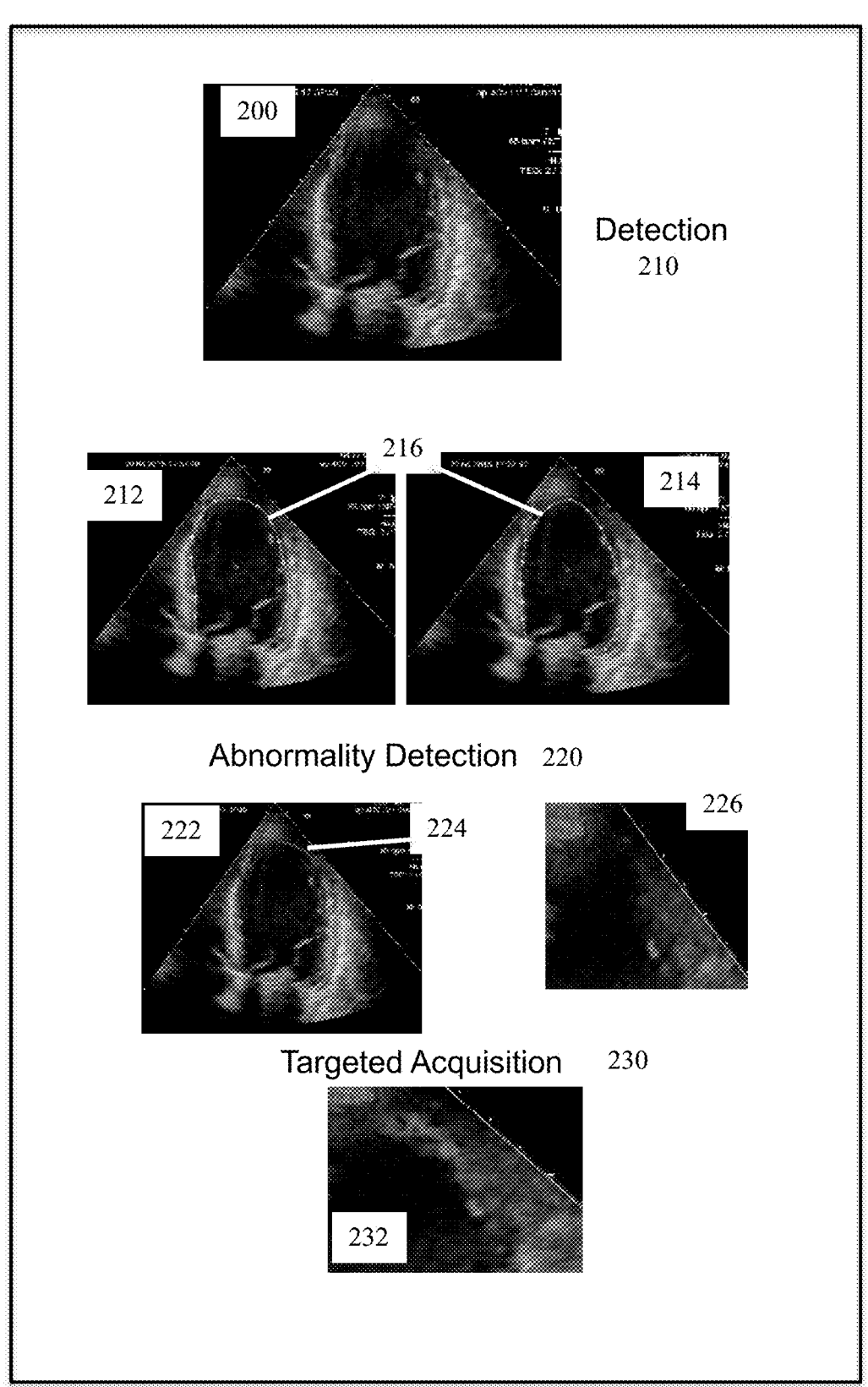
FIG. 2 illustrates abnormal motion detection with targeted scanning for a region of abnormal motion.

2D B-mode echocardiography data (e.g., images) are acquired for a plane in the heart, such as in one of the standard views (e.g., A2C). FIG. 2 shows a B-mode image 200 of a plane through a heart.

In act 110, an image processor detects abnormal wall motion from the ultrasound data resulting from the scanning of act 100. The ultrasound images from different times are used to detect abnormal wall motion. Image is used for ultrasound data from a scan in a display format or scan format prior to scan conversion. Data representing the patient that can or will be used to generate an image from an ultrasound scan is used as image data. The detection uses images from different times during the heart cycle, such as multiple images of standardized views.

After obtaining the best or acceptable quality images for a 2D view, the image processor detects the endo- and/or epicardial boundary (e.g., myocardium border). FIG. 2 shows an example where the boundary 216 is detected in act 210 in ED and ES images 212, 214. Any detection may be used, such as by random walker, thresholding, or pattern or model fitting. In one implementation, a machine learning algorithm or machine-learned model detects the boundary 216. Detection is performed for each of the images at other times in the heart cycle. In another implementation, the boundary 216 is detected on an ED frame or image automatically. The detected boundary 216 is tracked in the other frames, such as using speckle or local feature tracking (e.g., optical flow, motion prior, or speckle tracking). The result is the boundary 216 being located in each of the images of a heart cycle.

Any locations along the boundary 216 with abnormal motion are detected in act 220 (act 110). For example, the global and regional strains are calculated from tracked points along the boundary 216. Example tracked points are shown as white dots in images 212, 214 of FIG. 2. The strains indicate lengthening or shortening of the boundary between points over a given part of the heart cycle, such as ED-ES. A strain greater or less than a threshold may indicate abnormal motion. A machine-learned model or image processing may be used to detect the abnormal motion. Segment boundaries with abnormal motion are identified. The segments or regions of abnormal motion may be larger or smaller than standard segments used in a bull-eye visualization, such as the standard six segment division. None, one, or more regions of abnormal wall motion are detected. For example, myocardium boundary regions with abnormal motion, if any, are selected. The strains from regions of normal operation are calculated and may be saved for use in a strain map (e.g., bulls-eye model).

The abnormality may be due to actual poor heart wall motion or may be due to poor tracking. FIG. 2 shows an example. The abnormality detection of act 220 detects a region 224 of abnormal wall motion. As shown in image 222 and highlighted in the zoomed in portion 226 of image 222, there is lack of B-mode return in this region 224. There is little speckle. The resulting tracking to find the boundary 216 may be inaccurate, resulting in incorrect strain calculation and corresponding indication of abnormal wall motion.

To improve the strain calculation for the region 224, a further targeted acquisition is provided in act 230. The targeted acquisition may acquire an image 232 with more B-mode return, such as speckle, for the region 224. The acquisition is focused to and targeted at the region 224. A smaller field of view and corresponding settings are used to acquire better data for tracking and/or strain calculation in the region rather than the entire view of the heart chamber.

In act 120 of FIG. 1, the ultrasound scanner scans the region 224. Different regions 224 of detected abnormal wall motion may be scanned as separate patches. The scanning results in ultrasound data or images representing the region 224 over time in one or more heart cycles.

The ultrasound scanner is configured by values of settings (e.g., acquisition parameters) for scanning a region 224 or patch. The values for act 120 are different than used in act 100. For example, a smaller field of view or patch is scanned. The depth, width, focus, and/or scan pattern is different, such as only scanning a sub-area of the area of the image 200. The field of view is set to just cover the region 224 of the abnormal wall motion. This region 224 is less than the whole boundary 216 and corresponding original image 200. The gain, contrast, or other settings may be the same or different. Different combinations of values may be attempted to identify the combination providing the desired or optimum ultrasound data, such as to increase speckle or landmark information used in tracking. The values for the patch or region 224 are set to generate speckle in the resulting image 232.

Figure 3:
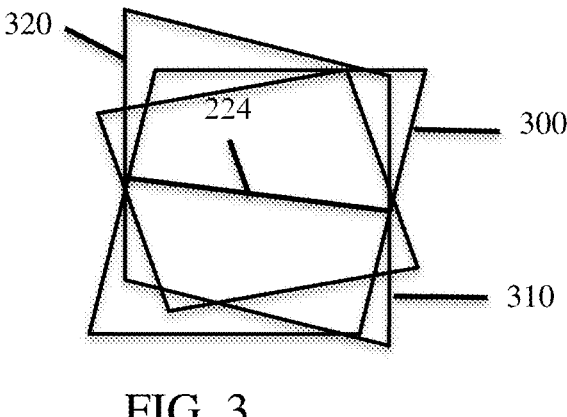
FIG. 3 illustrates different planes for scanning to acquire ultrasound data for strain determination.

In one implementation, the field of view is altered by changing the orientation of the scan plane relative to the region 224 and/or heart of the patient. The B-mode data is acquired with the patch or scan plane being a different plane than used for the scanning of act 100. For example, the scan plane is rotated for the region 224 to be at a non-zero angle to the plane of the standardized view acquired in act 100. FIG. 3 shows an example. The region 224 is originally scanned in plane 300. The scan plane is rotated to a different plane 310 for scanning the patch about the region 224. By scanning in a different plane, more speckle may result for the patch image 232 than for the region 224 of the original image 222 (see portion 226). Alternatively, or additionally, there is less out-of-plane motion at the boundary 216 in the different plane, so more accurate motion of the heart wall is detectable.

Any amount of rotation may be used. One or more rotated scan planes 310, 320 may be used, such as sampling (e.g., scanning) at different rotations and corresponding planes 310, 320. The result is additional data or samples that may be used to improve accuracy and/or finding an optimal or better scan plane for the region 224. Alternatively, only one rotation and corresponding scan plane are used.

The transducer may be capable of automated rotation. For example, a robot controlling the transducer rotates the transducer. As another example, electronic steering of a helical array or a multi-dimensional (2D) array is used. In another example, a mechanical rotation of the array, such as in a trans-esophageal probe, is used. Alternatively, instructions for rotating are output to the sonographer, and the sonographer then manually rotates the array to scan along the different plane and corresponding field of view.

In one implementation, the user is guided to acquire higher quality images in the vicinity of such detected region 224 by optimizing machine or acquisition parameters and/or rotating the imaging planes. The system recommends the user to rotate the probe in certain degrees and quantifies the motion only in this selected region 224. The probe or array is rotated by a specified degree suggested by the system, which analyzes the motion patterns and then estimates the next best possible location. The optimal orientation plane may be automatically determined by minimizing out of plane motion (e.g., find plane showing the largest amount of motion) and/or improving the quality of speckle patterns, which leads to improved tracking and motion field estimation. For example, if an abnormal motion region 224 is close to the apex and speckle moves towards the apex, it is difficult to track such speckle accurately. A better orientation plane improves the tracking in such selected location or region 224, and tracking can be done in real time since the images 232 contain just the small, selected region 224.

In another implementation, the user or image processor adjusts the settings (e.g., values of acquisition parameters) in the ultrasound scanner until better, improved, more, or sufficient speckle patterns are visible in the selected area. Speckle may be measured by a machine-learned model and/or by a measure of variance. The resulting improved ultrasound data may be used to verifying that the abnormality was not due to the low imaging quality in such region. Strain measurements for the region 224 are updated by running tracking only on the selected region 224 using the targeted acquisition images 232. The resulting strain is fused or collected with the previously determined strains for segments or regions without abnormal wall motion. The accuracy of segmental strains is improved due to the improved image quality. If it is not possible to acquire higher quality data in such region due to other reasons, having the additional data as additional sampling may result in more accurate strain determination.

In act 130, the image processor selects the values of the setting providing a most or more accurate tracking, strain, and/or analysis. Where multiple different combinations of values are sampled, the one providing sufficient or better ultrasound data is selected. The level of speckle and/or out-of-plane motion is measured in one approach. In one example, different scan planes at corresponding different orientations to the region 224 may result in different levels of speckle and/or out-of-plane motion. By maximizing speckle content and/or minimizing out-of-plane motion (maximizing in-plane motion), improved ultrasound data for tracking and/or strain determination is provided. The values of the settings resulting in the best available or sufficient (above/below a threshold) are selected. For example, the field of view in one plane is selected over another plane based on the level of scatter and/or amount of relative motion of the cardiac wall. The selection of values is a selection of the ultrasound data to use for tracking or strain determination, or vice versa.

Alternatively, no selection is performed. The ultrasound data from only one attempted different set of values is used, or data from any sampling are used together (e.g., calculate strain or wall position from each and average the results).

In act 140, the image processor determines the strain for the abnormal wall motion. The ultrasound data from the targeted acquisition of act 120, 230 is used to determine the strain. Patches of B-mode data of the region 224 from different times in the heart cycle are used to track the border 216, from which the strain is calculated. Since improved data is used, the resulting tracking and/or strain may be more accurate. Data from the selected plane and/or combination of values of settings are used for the tracking and strain determination. Data from other combinations of values of the settings may not be used or are additionally used (e.g., average results).

The strain is determined for the region 224. This strain may be interpolated, extrapolated, and/or used for the segment of a multi-segment model. The region 224 may be at a different location and/or be a different size than a segment of the multi-segment model, so the corresponding strain for the region is used or altered to be used for representing the segment.

In another implementation, the sampling on one or more planes in addition to the original plane is used. A multi-dimensional strain is determined. For example, the strain as a vector in three dimensions is determined using the data of different planes. The motion is tracked along different planes. As a result, the strain in three dimensions is determined.

FIG. 1 shows feedback from act 140 to act 120. Where the image processor detects multiple regions 224 in a given view (e.g., image 200 with corresponding images 212 and 214 for different times), the targeted scanning of act 120, selection of act 130, and determination of strain of act 140 are repeated for each of the regions 224. The scanning of the patch and determination of strain for that patch are repeated to provide improved strain for each region 224. The repetitions occur until strain is determined for each of the regions of abnormality. The same process is followed for all abnormal segments.

FIG. 1 also shows feedback from act 140 to act 100. For the multi-segment bulls-eye model, different segments may be from different views. Acts 100, 110, 120, 130, and 140 are repeated for each of the views (e.g., A4C, A3C, and A2C). For each standard or non-standard view, the scanning of act 100, detection of regions 224 of abnormal wall motion in act 110, targeted scanning of a patch or patches around each region of act 120, selection of act 130, and determination of strain 140 are repeated.

This tracking-based guidance continues until the full the scope of abnormal wall motion region is covered. The bulls-eye visualization is updated from the additional strain computations. Alternatively, a 3D motion field is constructed by fusing tracked motion or strain from different orientations. A 3D surface tracking is performed, and 3D strain measurements may be computed.

In act 150, the image processor outputs strain. The output is an image output to a display, computer network transmission, or memory.

The image represents the strain. The strain may be represented as text, graphic, highlighting, annotation, or other presentation. In one implementation, the image is a multi-segment model that includes the strain. For example, a 16, 17, or 18-segment bulls-eye view or model is used. The strain for each segment and a global strain are represented as color and/or alphanumerically. The strain may be used for scoring, so that the output scores reflect the strain. Other strain maps may be used. The strains in a given strain map may include one or more strains determined from a standard view and one or more strains determined from re-scanning or targeted scanning of patches using different values for scan settings. For example, a 17-segment model is a strain map having the strain determined from the B-mode data for the patch (e.g., from scan 120) for one segment and a second segment of the strain map having another strain determined from the standardized view (e.g., from scan 100). The strains determined from different data may be fused together (e.g., presented together) to better quantify the scope of the abnormal wall motion region. The targeted scanning may improve the strain map (e.g., of a 17-segment model) since dense strain values are now available inside each segment of the map instead of values that come from fusing only two neighboring views. Furthermore, more reliable four-grade scoring is constructed for a quick assessment of pathologies and motion abnormalities.

In another implementation, the image processor generates a multi-dimensional strain map for display. Volume, surface, or other three-dimensional rendering is used. The strains may be from different views. Some of the strains may be from scans along different planes. These strains from different planes provide a 3D map or vector of strain. 3D surface tracking may be applied to any multi-plane acquisitions to produce a 3D strain map only in the selected region. For these regions, higher accuracy may be provided. Full 3D B-mode echocardiography has lower temporal and spatial resolution than 2D and requires longer analysis time, so providing 3D strain or tracking for specific sub-sets or regions is used. Alternatively, a graph of strain vectors or another image showing strain in different dimensions is displayed.

FIG. 5 shows one embodiment of a system for detecting cardiac wall motion. By re-acquiring ultrasound data for suspect patches with different acquisition settings, cardiac wall motion may be more accurately determined.

The system implements the acts of FIG. 1. For example, the ultrasound scanner 400, using the beamformer 408 and transducer 410, performs the scans of acts 100 and 120. The image processor 402 implements the acts 110, 130, and 140 with output of the strain of act 150 being to the display 420. Alternatively, the system implements different, additional, or fewer acts.

The system includes a medical diagnostic ultrasound scanner 400, releasable transducer 410, display 420, and an ECG device 430. Additional, different, or fewer components may be provided. For example, a processor outside the ultrasound scanner 400 for analyzing ultrasound data is provided. As another example, the ECG device 430 is integrated within the ultrasound scanner 400. In yet another example, the ECG device 430 is not provided as the ultrasound scanner 400 uses ultrasound data to determine the heart cycle characteristics (e.g., interval).

The ECG device 430 is a processor, circuit, and/or electrodes. Any now known or later developed ECG device may be used. By placing the electrodes on a patient, the heart trace of the patient's heart cycle is generated. The ECG device 430 detects the R-waves, other phases, interval, and/or heart rate of the heart cycle. Alternatively, the ultrasound scanner 400 detects the phases of the heart cycle from a trace signal received from the ECG device 430.

The ultrasound scanner 400 is a medical diagnostic ultrasound imaging system. In other embodiments, the ultrasound scanner 400 is a therapy system that may also image. Any now known or later developed system for cardiac echocardiography may be used. The ultrasound scanner 400 is configured by settings for performing cardiac echocardiography of a patient. During an imaging session, the transducer array 410 is positioned to scan the heart of the patient, and images are generated over one or more heart cycles.

The ultrasound scanner 400 includes the transducer array 410, a beamformer 408, an image processor 402, the display 420, an input 406, the image processor 402, and a memory 404. Additional, different, or fewer components may be provided. For example, the transducer array 410 and/or display 420 are separate from the scanner 400. As another example, the memory 404 is remote or not part of the ultrasound scanner 400. As yet another example, a scan converter, temporal filter, spatial filter, or another ultrasound imaging component is provided.

The transducer array 410 is an array of transducer elements in a housing. The housing is adapted or shaped for handheld use on the exterior of the patient. Alternatively, the housing is shaped as a catheter, intraoperative probe, intercavity probe, transesophageal probe, or other now known or later developed transducer probe. The array is a linear, multidimensional, annular or other now known or later developed array of piezoelectric or microelectromechanical elements.

The transducer array 410 generates acoustic energy in response to electrical signals from the beamformer 408. For imaging, acoustic echoes received by the transducer array 410 are transduced into electrical signals, and the transducer array 410 provides the electrical signals to the beamformer 408.

The beamformer 408 is a transmit beamformer, receive beamformer or both transmit and receive beamformer. As a transmit beamformer, the beamformer 408 includes waveform generators or pulsers, delays, phase rotators, timing generators, amplifiers, combinations thereof or other now known or later developed transmit beamformer components in a plurality of channels. For transmission, the beamformer 408 generates relatively delayed and apodized waveforms for each of a plurality of channels for a corresponding plurality of transducer elements. The transducer array 410 forms an acoustic beam or beams in response to the waveforms.

As a receive beamformer, the beamformer 408 includes channels with delays, phase rotators, amplifiers, or combinations thereof and includes a summer or summers for adding the signals from each channel together. For reception, the beamformer 408 generates samples representing different spatial locations.

The receive beamformed samples are provided to the image processor 402 for generating an image. The image processor 402 is a detector, filter, scan converter, three-dimensional processor, combinations thereof or other now known or later developed image generator. The detection is B-mode (intensity. The samples are detected, scan converted, and provided to the display 420. Other image processing may be applied.

The ultrasound scanner 400, including the beamformer 408, transducer array 410, and/or the image processor 402 operate pursuant to values of settings. Various acquisition parameters are set to establish a field of view, contract, gain, and/or other characteristics of imaging. The ultrasound scanner 400 is configured to scan or acquire ultrasound data based on the values of the settings.

The ultrasound scanner 400 is configured to scan a heart of a patient. For example, using manual guidance and/or automated detection, the heart is scanned to identify a standardized view. A sequence of images over one or more heart cycles of the view are acquired by scanning. The values of the settings define the scanning and image processing to acquire the ultrasound data.

The ultrasound scanner 400 is configured to scan targeted patches. One or more locations within an initial view are scanned in a more targeted manner. The values of the settings are altered to re-scan a localized region, such as a region showing abnormal heart motion. The field of view, gain, contrast, or other settings are altered to scan a patch about a region.

The input 406 is a user input device, such as a keyboard, touchscreen, trackball, mouse, buttons, rotatable knobs, and/or sliders. The input allows for sonographer input of values of settings to configure the ultrasound scanner 400. Other user input information may be input, such as for detection of abnormal regions and/or indication or selection of improved imaging.

The image processor 402 is a general processor, digital signal processor, controller, artificial intelligence processor, application specific integrated circuit, field programmable gate array, analog circuit, digital circuit, combinations thereof, or another now known or later developed device for tracking, determining strain, configuring the ultrasound scanner 400, and/or generating a strain image. The image processor 402 is configured by hardware, software, and/or firmware to detect abnormalities, select settings, determine strain, and/or output an image.

The image processor 402 is configured to detect a location of abnormality of the cardiac wall motion for a patient. Ultrasound data from a scan, such as a scan of a standardized view of the heart, is used to detect a region where there is abnormal cardiac wall motion, such as due to actual abnormality or due to poor data quality.

The image processor 402 is configured to determine strain of the cardiac wall motion at various locations along the cardiac wall. The image processor 402 detects the wall, such as using artificial intelligence. The image processor 402 tracks locations along the wall through the sequence of images, providing cardiac wall motion. The image processor 402 calculates strain from the tracking or wall motion. The strains may be determined for different regions or segments in the original views.

Where abnormal wall motion is detected, the image processor 402 is configured to cause the ultrasound scanner 400 to scan a targeted patch about the region of abnormal wall motion. Different values of one or more settings are used to acquire improved ultrasound data for the patch or region. The ultrasound data is acquired from the scan using at least one of the different values of the one or more settings as compared to the values of the settings for the original view.

The values may define a different scan plane to use for scanning the region. The image processor 402 may control the ultrasound scanner 400 to scan the different plane for the patch and/or may instruct the sonographer to change an orientation of the transducer array 410. The region is scanned in two or more different planes based on the control by the image processor 402. Other settings, such as gain and/or contrast, may be different instead or in addition to the field of view (depth, azimuth extent, and/or scan plane) for the re-scan of the patches. The use of different values of settings may result in different levels of speckle and/or out-of-plane motion. The ultrasound data with greater speckle and/or lesser out-of-plane motion is used by the image processor 402 to determine the strain for that region.

The display 420 is a monitor, liquid crystal display, plasma display, light emitting diode display, printer, projector, or other device for outputting one or more images for viewing. Any now known or later developed display device may be used. The display 420 is part of the ultrasound scanner 400, but may be a remote device, such as a wall mounted or remote workstation display.

The display 420 shows one or more images of the patient's heart. The images are generated as part of cardiac echocardiography. During the cardiac echocardiography, the ultrasound scanner 400 may also output guidance, such as rotation of the transducer array 410 on the display 420.

The display 420 shows one or more images with strain information. An image of the strain is generated by the image processor 402 and output by the display 420. The image of strain may be a bulls-eye view from a multi-segment model. Other strain maps showing strain as a function of location along the heart wall may be output. A 3D surface strain may be output, such as by surface or volume rendering.

The memory 404 is a non-transitory computer readable storage medium, such as a cache, buffer, RAM, removable media, hard drive or other computer readable storage media. Computer readable storage media include various types of volatile and nonvolatile storage media. The memory 404 stores ECG data, tracking, strain, detected boundaries, abnormal regions, artificial intelligence (e.g., machine-learned model 405), strain image, or other information for guidance of cardiac echocardiography. Input, output, and/or information being processed is stored.

The memory 404 or another memory stores instructions for the image processor 402 and/or other processors. Data representing instructions executable by a programmed processor for stress echocardiography guidance is stored in the memory. The instructions are for implementing the processes, methods and/or techniques discussed herein. The functions, acts or tasks illustrated in the figures or described herein are executed in response to one or more sets of instructions stored in or on the computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for detecting cardiac wall motion with a medical ultrasound scanner, the method comprising:

first scanning, by the medical ultrasound scanner using first values of scan settings, a first plane through a heart of a patient, the first plane scanned at different times providing first ultrasound data representing the heart at the different times;

detecting, by an image processor of the medical ultrasound scanner, abnormal wall motion from the first ultrasound data, the image processor identifying an indication of the abnormal wall motion from a detected endo- and/or epicardial boundary represented in the first ultrasound data; then in response to detecting the abnormal wall motion, second scanning, by the medical ultrasound scanner using second values of the scan settings, a region of the abnormal wall motion in a second plane, the second values of the scan settings different than the first values of the scan settings, the second plane different than the first plane, the second scanning resulting in second ultrasound data; then determining, by the image processor of the medical ultrasound scanner, strain for the abnormal wall motion as a calculation of the strain from the second ultrasound data; and displaying an image representing the strain.

2. The method of claim 1 wherein first scanning comprises first scanning of a standardized view of the heart, and wherein the second scanning comprises second scanning with a smaller field of view just covering the region of the abnormal wall motion, the region less than a field of view of the standardized view.

3. The method of claim 1 wherein detecting comprises detecting with a machine-learned model.

4. The method of claim 1 wherein the scan settings comprise gain, contrast, depth, and/or field of view.

5. The method of claim 4 wherein the scan settings comprise the field of view, the first values being for a larger field of view than the second values, the first values being for the first plane, and the second values being for the second plane.

6. The method of claim 1 further comprising selecting the second plane based on a level of scatter and/or amount of relative motion of the cardiac wall.

7. The method of claim 1 further comprising third scanning the region in a third plane different than the first and second planes.

8. The method of claim 1 wherein second scanning comprises second scanning with the second values configuring the medical ultrasound scanner for generating speckle.

9. The method of claim 1 wherein determining the strain comprises determining the strain for a segment of a multi-segment model, and wherein displaying comprises displaying the multi-segment model including the strain.

10. The method of claim 1 wherein determining the strain comprises determining the strain in multiple dimensions for the first and second planes, and wherein displaying comprises displaying a multi-dimensional strain map.

11. The method of claim 1 further comprising repeating the second scanning and determining for different regions of different abnormal wall motion.

12. The method of claim 1 further comprising repeating the first scanning, detection, second scanning, and determining for different standardized views of the heart, and wherein displaying comprises displaying the strains from the different standardized views.

13. An ultrasound system for detecting cardiac wall motion, the system comprising:

an ultrasound scanner comprising a processor configured to (i) detect a location of abnormality of the cardiac wall motion for a patient, the detection of the location comprising identification of an indication of the abnormality from a detected endo- and/or epicardial boundary, then (ii) scan the location with different values of one or more settings than first values of the settings used for the detection of the location, wherein the scan is focused and targeted at the detected location, and (iii) determine strain of the cardiac wall motion at the locations from ultrasound data from the scan using at least one of the different values of the one or more settings than the first values used for the detection of the location; and a display configured to display an image of the strain.

14. The ultrasound system of claim 13 wherein the one or more settings are for scan of different planes such that the ultrasound scanner is configured to scan the location in the different planes.

15. The ultrasound system of claim 13 wherein the one or more settings are gain, contrast, and/or depth such that the ultrasound scanner is configured to scan the location for imaging with different levels of speckle.

16. The ultrasound system of claim 13 wherein the ultrasound scanner is configured to scan a heart of the patient in a standardized view, detect the location from the standardized view, and scan the location with a field of view less than the standardized view.

17. A non-transitory computer readable storage medium having stored therein data representing instructions executable by a programmed processor for detecting cardiac wall motion, the storage medium comprising instructions for:

scanning a heart of a patient in a standardized view;

detecting abnormal wall motion of the heart from the standardized view, the detecting of the abnormal wall motion comprising identifying by the programmed processor an indication of an abnormality from a detected endo- and/or epicardial boundary;

acquiring B-mode data in a patch at the abnormal wall motion, a size of the patch for scanning as part of the acquiring being less than what was used for the scanning of the heart in the standardized view, the size targeted on a region of the abnormal wall motion;

determining strain from the B-mode data for the patch; and displaying a strain map including a first segment of the strain map having the strain determined from the B-mode data for the patch and a second segment of the strain map having another strain determined from the standardized view, the strain determined form the B-mode data for the patch being from the scanning as part of the acquiring and the strain determined from the standardized view being from the scanning of the heart of the patient in the standardized view such that the strains are calculated from different scans.

18. The non-transitory computer readable storage medium of claim 17, wherein the instructions for acquiring the B-mode data in the patch comprises acquiring the B-mode data with the patch being in a different plane than the standardized view, the instructions further comprising selecting the different plane based on an amount of speckle or motion.

19. The non-transitory computer readable storage medium of claim 17, wherein the instructions for acquiring the B-mode data comprises acquiring the B-mode data with a greater level of speckle in the patch than in the standardized view at a location of the abnormal wall motion.

20. The non-transitory computer readable storage medium of claim 17, wherein the instructions further comprise repeating the scanning, detecting, acquiring and determining for different standardized views, and wherein the instructions for displaying the strain map comprises displaying a 16, 17, or 18-segment bulls-eye view.

* * * * *